United States Patent [19]

Kilgore

[11] Patent Number: 5,782,779
[45] Date of Patent: Jul. 21, 1998

[54] VIBRATING TAMPON APPARATUS

[76] Inventor: Steven A. Kilgore, 910 Ward Rd., Raymore, Mo. 64083

[21] Appl. No.: 862,214

[22] Filed: May 23, 1997

[51] Int. Cl.[6] .................................................. A61H 21/00
[52] U.S. Cl. ............................ 601/70; 601/72; 604/904
[58] Field of Search ............................ 601/46, 67, 69, 601/70–72, 78, 80, 81; 604/904, 363

[56] References Cited

U.S. PATENT DOCUMENTS

| | | |
|---|---|---|
| 2,422,639 | 6/1947 | Wenander . |
| 3,451,391 | 6/1969 | Tavel ........................................ 601/72 |
| 3,626,931 | 12/1971 | Bysakh . |
| 3,669,100 | 6/1972 | Csanad . |
| 4,878,489 | 11/1989 | Kamayachi ............................ 601/72 |
| 5,067,480 | 11/1991 | Woog et al. . |
| 5,573,499 | 11/1996 | McAllister ............................ 601/70 |

FOREIGN PATENT DOCUMENTS 472965  3/1992  European Pat. Off. ................. 601/70

*Primary Examiner*—Danton D. DeMille
*Attorney, Agent, or Firm*—Henderson & Sturm

[57] ABSTRACT

A vibrating tampon apparatus 10 for easing a woman's menstrual cramps wherein the apparatus 10 includes an inner vibrator unit 12 and an outer tampon unit 11 surrounding the vibrator unit 12 which includes a vibrator motor 36 which is actuated by a tampon string 25 for imparting vibratory motion to the apparatus 10.

8 Claims, 1 Drawing Sheet

U.S. Patent     Jul. 21, 1998     5,782,779
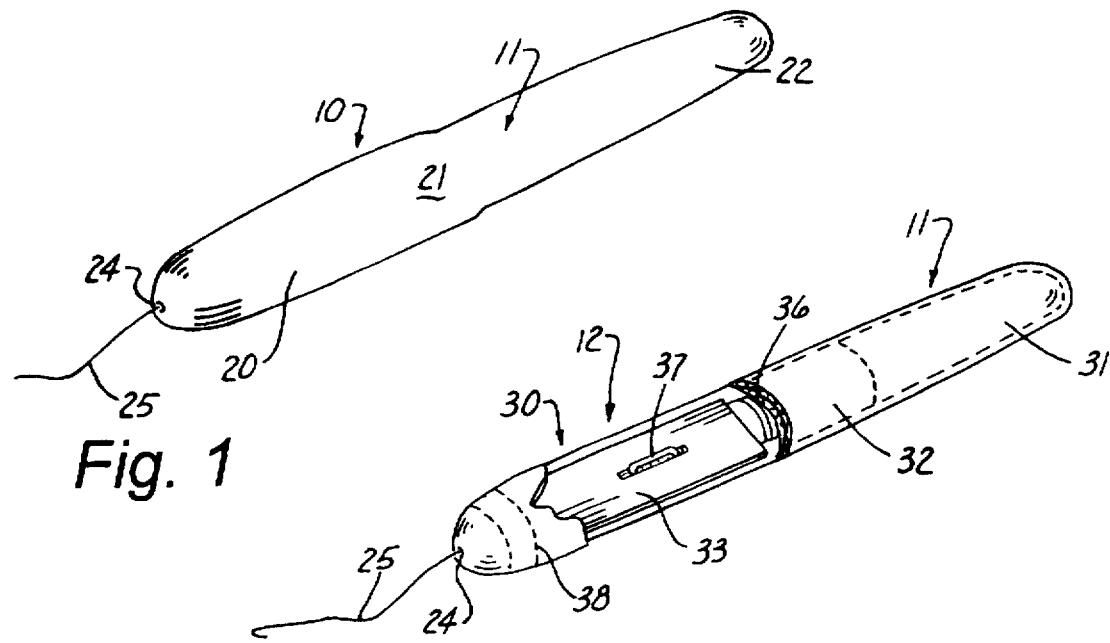
Fig. 1
Fig. 2
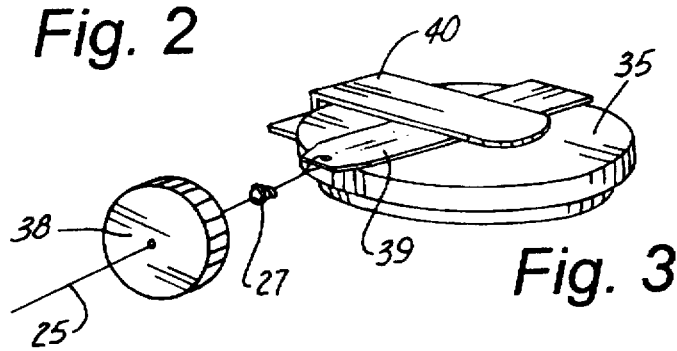
Fig. 3
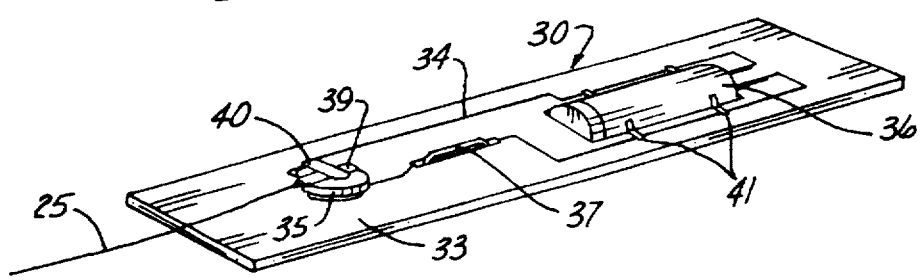
Fig. 4
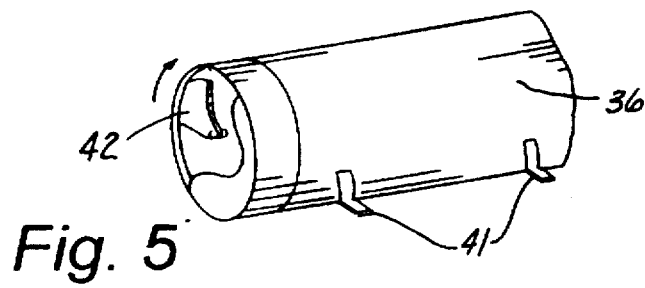
Fig. 5

VIBRATING TAMPON APPARATUS

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to the field of sanitary napkin constructions in general, and in particular to a sanitary napkin/tampon construction having a vibrating mechanism operatively associated therewith.

2. Description of Related Art

As can be seen by reference to the following U.S. Pat. Nos. 2,422,639; 3,626,931; 3,669,100; and 5,067,480 the prior art is replete with myriad and diverse vibrating devices.

While all of the aforementioned prior art constructions are more than adequate for the basic purpose and function for which they have been specifically designed, they are neither designed nor intended to perform the dual function that is provided by the subject matter that forms the basis of the present invention.

As many women who suffer menstrual cramps are aware, stimulation of the vaginal tract can under certain circumstances alleviate the pain associated with menstrual cramping. In addition, many women experience vaginal dryness at this time which makes the insertion of a tampon a trying experience.

As a consequence of the foregoing situation, there has existed a longstanding need for a new and improved tampon construction that contains an internal vibrator mechanism wherein the vibrating action will not only facilitate the insertion of the tampon into the vaginal tract, but which may also under certain circumstances minimize the effects of menstrual cramps. The provision of such a construction is a stated objective of the present invention.

BRIEF SUMMARY OF THE INVENTION

Briefly stated, the vibrating tampon apparatus that forms the basis of the present invention comprises a tampon with a built-in, miniature battery operated vibrating mechanism which may assist a woman by easing menstrual cramps.

The apparatus resembles conventional cotton tampons, including the removal string, but differ greatly on the inside as they contain an internal vibrating motor and self-contained, safe power source. The interior mechanism is housed inside of a non-toxic polyethylene plastic tube which is ultrasonically welded together providing a liquid proof container. This keeps liquids from entering or exiting the interior apparatus.

The mechanism located inside of the case consists of a printed circuit board assembly with an associated battery, micro-fuse and, as mentioned previously, a miniature vibrating motor. This mechanism provides for a complete assembly which fits conveniently inside of the non-toxic tube component. The tampon string is connected to a flat, plastic polyethylene insulator which fits between the battery and the battery contact. The insulator keeps the battery contact from connecting with the positive terminal of the button-type battery, keeping voltage from reaching the vibrating motor.

A micro-fuse is located between the battery power source and the motor, and is designed to disconnect power from the battery to the vibrating motor if the motor should ever develop the slightest short. Once the printed circuit board assembly is installed inside of the plastic tube component, the activation/removal string is fed through a very small hole in the front of the apparatus. The string, as previously mentioned, is connected to the flat, plastic insulator, also has a string limiting knot between the battery and the interior washer. The interior washer serves the purpose of limiting the distance that the string may be pulled, while providing a liquid-type exit for the string. The string functions in this manner: the string is first pulled before use, which removes the insulator from between the battery and the battery contact, activating the vibrating motor The string can only go far enough to pull the insulator out of the way before the limiting knot makes contact with the interior washer, stopping and limiting the string from going any further while providing the user with a familiar means of removing the tampon.

The exterior of the tampon is woven with dense cotton, similar to a conventional tampon. The apparatus once activated by pulling the string, is inserted using a conventional cardboard applicator, which has been in use for decades and does not represent new technology.

In use, a user would insert the tampon be removing the outer sheath in the standard manner. Next, the user would activate the unit by pulling the pull-string, and the user would insert the tampon in a standard manner. The battery is designed to last for twenty minutes. Since the apparatus is disposable, the user would remove the tampon in the standard manner and discard. The use of the apparatus would provide the user with relief from painful menstrual cramps during times of menstruation.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein:

FIG. 1 is a perspective view of the exterior of the vibrating tampon apparatus that forms the basis of the present invention;

FIG. 2 is a partial cut-away view of the apparatus showing a portion of the vibrator unit;

FIG. 3 is an isolated detail of the string actuator portion of the invention;

FIG. 4 is a perspective view of the vibrator mechanism and associated circuitry; and FIG. 5 is an isolated detail view of a portion of the vibrator motor.

DETAILED DESCRIPTION OF THE INVENTION

As can be seen by reference to the drawings, and in particularly to FIG. 1, the vibrating tampon apparatus that forms the basis of the present invention is designated generally by the reference number 10. The apparatus 10 comprises in general, an outer tampon unit 11 and an inner vibrator unit 12. These units will now be described in seriatim fashion.

As can best be seen by reference to FIGS. 1 and 2, the outer tampon unit 11 comprises an elongated tampon member 20 fabricated from a sterile absorbent material 21 such as cotton or the like. The tampon member 20 forms a fabric envelope 22 which surrounds the vibrator unit 12.

In addition, one end 23 of the tampon member 20 is provided with a discrete aperture 24 which is dimensioned to receive a pull string element 25 whose purpose and function goes beyond that of a conventional tampon string, as will be explained in greater detail further on in the specification.

As shown in FIG. 2, the vibrator unit 12 comprises a generally elongated vibrator member 30 including a male 31 and female 32 casing segment which are joined together in a well recognized fashion to provide a waterproof housing for the internal components of the vibrator member 30.

Turning now to FIGS. 3 through 5, it can be seen that the internal workings of the vibrator member 30 comprise a circuit board 33 having a printed circuit 34 which operatively connects a miniature battery power source 35 to a miniature vibrator motor 36 wherein a micro-fuse 37 is interposed between the power source 35 and the vibrator motor 36.

As can best be seen by reference to FIGS. 3 and 4, the tampon string 25 extends through an interior washer 38 disposed within one of the casing segments 32 and is operatively secured on its inboard end to a plastic insulator element 39 which is operatively disposed intermediate the battery holder contact 40 and the battery 35 per se to prevent current from passing from the battery 35 to the vibrator motor 36.

In addition, a knot 27 is formed on the inboard end of the tampon string 25 intermediate the insulator element 39 and the interior washer 38 to limit the distance that the insulator element 39 may be withdrawn relative to the interior washer 38 for reasons that will be explained shortly.

Turning now to FIGS. 4 and 5, it can be seen that the vibrator motor 36 is secured to the circuit board 33 by a plurality of mounting tabs 41 and one end of the vibrator motor 36 is provided with a motor counterweight 42 whose oscillating motion imparts a vibratory motion to the tampon member 20 via the external casing segments 31 and 32.

As was explained previously, the vibrating tampon apparatus 10 of the invention is activated by pulling the tampon string 25 to remove the insulator element 39 from between the battery holder contact 40 and the battery 35 to complete the electrical circuit to the vibrator motor 36. Once the insulator element 39 has been removed, the vibrator motor 36 will continue to operate for the life of the battery 35 (approximately twenty minutes) whereupon the apparatus 10 may be removed from the vaginal tract via the tampon string in a well recognized manner.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooded parts together, whereas, a screw employs a helical surface, in the environment of fastening wooden parts, a nail and a screw may be equivalent structures.

I claim:

1. A vibrating tampon apparatus comprising:

an inner vibrator member including a vibrator motor contained within a pair of casing segments;

an outer tampon member fabricated from a sterile absorbent material and disposed in a surrounding relationship relative to said inner vibrator member; and means for activating said vibrator motor.

2. The apparatus as in claim 1 wherein said means for activating said vibrator motor includes a tampon string which extends through one end of the tampon member and into the interior of one of the casing segments.

3. The apparatus as in claim 2 wherein said vibrator motor is electrically connected to a battery power source by an electric circuit board.

4. The apparatus as in claim 3 wherein said tampon string is connected on one end to an insulator element which is interposed between said battery power source and a battery contact.

5. The apparatus as in claim 4 further including:

means for limiting the movement of the insulator element relative to one end of the vibrator member.

6. The apparatus as in claim 4 further including:

an interior washer disposed within one of the casing segments and dimensioned to receive a portion of said tampon string.

7. The apparatus as in claim 6 wherein a knot is formed in said tampon string intermediate said interior washer and said insulator element to limit the rearward movement of the insulator element relative to said interior washer.

8. The apparatus as in claim 3 wherein said electric circuit board is provided with a micro-fuse.

* * * * *